US006685883B2

(12) United States Patent
Schianchi et al.

(10) Patent No.: US 6,685,883 B2
(45) Date of Patent: Feb. 3, 2004

(54) METHOD AND UNIT FOR STERILIZING PACKAGING SHEET MATERIAL FOR MANUFACTURING SEALED PACKAGES OF POURABLE FOOD PRODUCTS

(75) Inventors: Roberto Schianchi, Malmoe (SE); Håkan Möller, Lund (SE); Lars Näslund, Skattevägen (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 281 days.

(21) Appl. No.: 09/826,041

(22) Filed: Apr. 5, 2001

(65) Prior Publication Data

US 2001/0035500 A1 Nov. 1, 2001

Related U.S. Application Data

(63) Continuation-in-part of application No. 09/597,695, filed on Jun. 19, 2000, now abandoned.

(30) Foreign Application Priority Data

Aug. 27, 1999 (EP) ........................................... 99830534

(51) Int. Cl.[7] ................................................ A61L 2/00

(52) U.S. Cl. ........................ 422/22; 250/455.11; 422/1; 422/23

(58) Field of Search ................ 422/22, 23; 250/455.11

(56) References Cited

U.S. PATENT DOCUMENTS

| | | | | |
|---|---|---|---|---|
| 3,780,308 A | | 12/1973 | Nablo | 250/492 |
| 4,246,297 A | * | 1/1981 | Nablo et al. | 427/505 |
| 4,631,444 A | * | 12/1986 | Cheever | 313/420 |
| 5,194,742 A | * | 3/1993 | Avnery et al. | 250/492.3 |
| RE35,203 E | * | 4/1996 | Wakalopulos | 250/492.3 |
| 6,140,657 A | * | 10/2000 | Wakalopulos et al. | 250/492.3 |

FOREIGN PATENT DOCUMENTS

| | | |
|---|---|---|
| EP | 0 919 246 | 6/1999 |
| GB | 1 027 874 | 4/1966 |
| GB | 1 460 134 | 12/1976 |
| JP | 58-216528 | 12/1983 |

* cited by examiner

*Primary Examiner*—Krisanne Thornton
(74) *Attorney, Agent, or Firm*—Burns, Doane, Swecker & Mathis, L.L.P.

(57) ABSTRACT

A method and unit sterilizing sheet packaging material for producing sealed packages of pourable food products, the method including the step of directing on to opposite faces of the packaging material respective low-voltage electron beams, each having an energy of at most 100 keV. The unit includes generating devices for generating the low-voltage electron beams.

7 Claims, 2 Drawing Sheets

METHOD AND UNIT FOR STERILIZING PACKAGING SHEET MATERIAL FOR MANUFACTURING SEALED PACKAGES OF POURABLE FOOD PRODUCTS

This application is a continuation-in-part of U.S. application Ser. No. 09/597,695, filed Jun. 19, 2000 now abandoned the entire content of which is hereby incorporated by reference.

FIELD OF THE INVENTION

The present invention relates to a method and unit for sterilizing packaging sheet material for manufacturing sealed packages of pourable food products.

BACKGROUND OF THE INVENTION

As is known, numerous pourable food products, such as fruit juice, UHT (ultra-high-temperature processed) milk, wine, tomato sauce, etc., are sold in packages formed, on fully automatic packaging machines, from packaging sheet material, which may be constituted by pre-cut blanks or by a continuous web or strip of packaging material which is folded and longitudinally sealed to define a continuous, longitudinally sealed packaging material tube.

The packaging material may be constituted by a single or multi-layer plastics material, polymeric material, mineral-filled polymeric material or a laminated paperboard-type material. By way of example, one known type of paperboard-type packaging material has a multilayer structure comprising a layer of paper material covered on both sides with layers of heat-seal material, e.g. polyethylene. In the case of aseptic packages for long-storage products such as UHT milk, the packaging sheet material comprises a layer of barrier material defined, for example, by an aluminum film, which is superimposed on a layer of heat-seal plastic material and is in turn covered with another layer of heat-seal plastic material which eventually defines the inner face of the package contacting the food product.

For producing aseptic packages in conventional form, fill and seal-type packaging machines, the strip of packaging material is provided, e.g. unwound off a reel, and fed through a sterilizing unit in which it is sterilized, for example, by immersion in a bath of liquid sterilizing agent such as a concentrated solution of hydrogen peroxide and water.

More specifically, the sterilizing unit comprises a bath filled, in use, with the sterilizing agent in which the strip is fed. The bath conveniently comprises two parallel vertical branches connected at the bottom to define a U-shaped path of a length depending on the traveling speed of the strip and such as to allow enough time to treat the packaging material. For effective, fairly fast treatment, so as to reduce the size of the sterilizing chamber, the sterilizing agent must be maintained at a high temperature of, say, roughly 70° C.

The sterilizing unit also comprises an aseptic chamber in which the strip of packaging material issuing from the sterilizing bath is treated mechanically (e.g. by means of drying rollers) and thermofluidically (e.g. by means of hot-air jets) to remove any residual sterilizing agent. The amount of residual sterilizing agent allowed in the packaged product, in fact, is governed by strict standards (the maximum permissible amount being in the order of a 0.5 parts per million). The aseptic chamber must also be maintained slightly above ambient pressure to ensure any leakage through the seals occurs outwards as opposed to inwards of the chamber, to keep out any contaminating agents.

Before leaving the aseptic chamber, the strip is folded into a cylinder and sealed longitudinally to form in known manner a continuous, vertical, longitudinally sealed tube. The tube of packaging material, in fact, forms an extension of the aseptic chamber and is filled continuously with the pourable product and then fed to a forming unit for forming individual packages and by which the tube is gripped between pairs of jaws to seal the tube transversely and form aseptic pillow packs. The pillow packs are separated by cutting the sealed portions between the packs, and are then fed to a final folding station where they are folded mechanically into the finished form.

Alternatively, the packaging material is sterilized by applying, on the side of the packaging material eventually defining the inner face of the package, a thin film of hydrogen peroxide, which is later removed by heating. Sterilizing units are also known in which the hydrogen peroxide is applied to the surface of the packaging sheet material by liquid atomization or gas condensation.

Packaging machines of the above type are used widely and satisfactorily in a wide range of food industries, and performance of the sterilizing unit, in particular, is such as to amply conform with standards governing asepticity of the packages and residual sterilizing agent.

Within the industry, however, demand for further improvement exists, especially with regard to elimination of residual sterilizing agents, and which stems, in particular, from market demand for packages featuring reclosable opening devices which are easy to open and provide for easy pouring of the product.

In the case of non-aseptic packaging machines, such devices can be applied (e.g. injection molded) directly to the strip material before the packages are formed. Conversely, in the case of aseptic packaging machines, opening devices are normally applied after the packages are formed, which poses drawbacks from the production standpoint by requiring the use of sophisticated systems for supplying and applying the devices.

The above mentioned opening devices, if applied beforehand to the packaging sheet material, form breaks in the geometric continuity of the packaging sheet material, in which residual sterilizing agent may become trapped, and from which the sterilizing agent cannot be removed completely using known techniques.

On the other hand, using additional means to remove the sterilizing agent may have a negative effect on the operating parameters, in particular temperature and pressure, of the aseptic chamber, and impair performance of the sterilizing unit as a whole.

To eliminate the above drawbacks, sterilizing units have been devised using electron beams to irradiate moving sheet packaging material. More specifically, as known from SE-A-9503810, the sheet packaging material is irradiated on one face by an electron beam issuing from an accelerator located to one side of the packaging material. The electron beam penetrates the packaging material and so sterilizes both opposite faces simultaneously.

The above method, however, is not without drawbacks of its own, which mainly lie in alteration of the packaging material by passage of the electrons. More specifically, the packed product can acquire, from the packaging material, an unpleasant, so-called "off-flavor".

SUMMARY OF THE INVENTION

It is an object of the present invention to provide a method of sterilizing sheet packaging material for producing sealed packages of pourable food products, designed to provide an effective, straightforward, low-cost solution to the aforementioned problems.

According to the present invention, there is provided a method of sterilizing sheet packaging material for producing sealed packages of pourable food products, the method comprising the step of irradiating the packaging material with electrons, wherein the irradiating step comprises the step of directing on to opposite faces of the sheet packaging material respective low-voltage electron beams, each having an energy of at most 100 keV.

The present invention also relates to a unit for sterilizing sheet packaging material for producing sealed packages of pourable food products, the unit comprising generating devices for generating low-voltage electron beams, which are located on opposite sides of the sheet packaging material and generate respective electron beams directed on to opposite faces of the packaging material and each having an energy of at most 100 keV.

BRIEF DESCRIPTION OF THE DRAWINGS

Preferred embodiment/s of the invention is/are disclosed in the following description and illustrated in the accompanying drawings, in which.

DETAILED DESCRIPTION OF THE INVENTION

Figure 1:
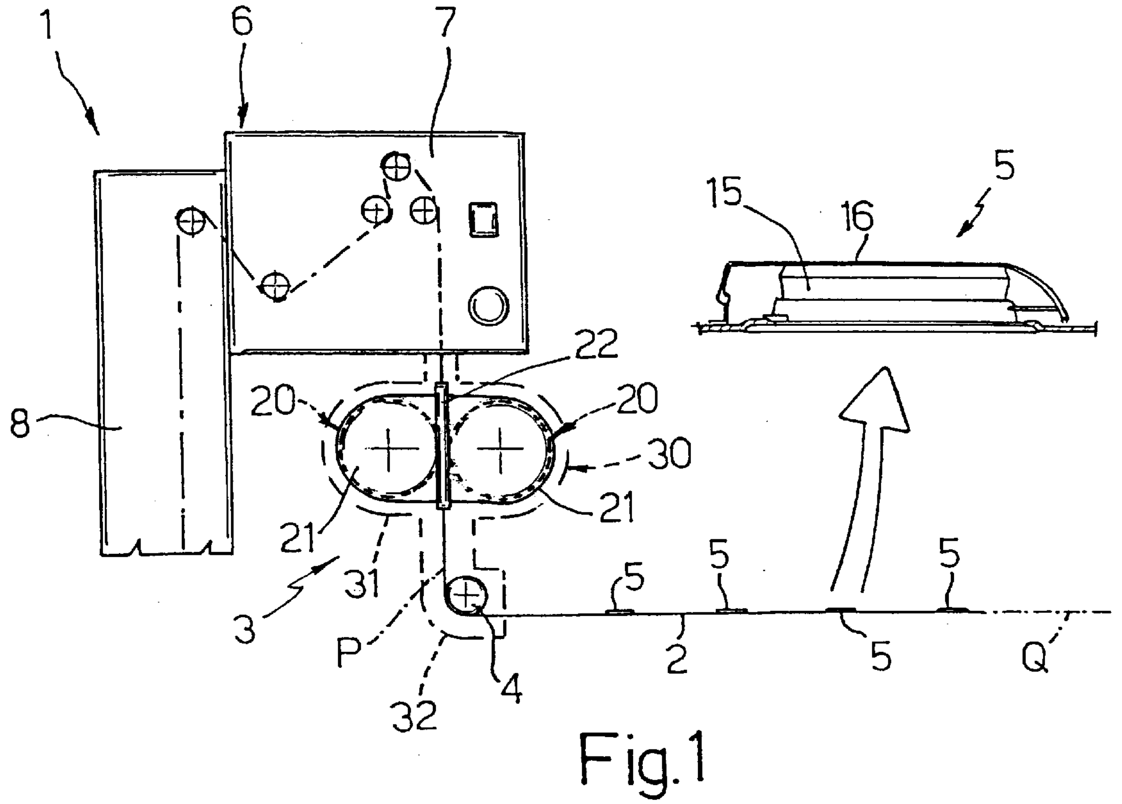
FIG. 1 shows a lateral elevation of a portion of a packaging machine for producing aseptic sealed packages of pourable food products and featuring a sterilizing unit in accordance with the present invention.

Reference number 1 in FIG. 1 indicates as a whole a packaging machine for producing aseptic sealed packages (not shown) of pourable food products from a packaging sheet material 2.

Machine 1 comprises a sterilizing unit 3 for sterilizing the packaging sheet material 2, which is fed, for example, off a known reel (not shown) along a substantially vertical path P. More specifically, on leaving the reel, packaging sheet material 2 is fed, in the illustrated example, along a substantially horizontal path Q and is detoured along vertical path P by a guide roller 4.

To produce packages with pre-applied auxiliary items, such as reclosable opening devices 5 of plastic material—e.g. of the type illustrated in International Patent Application WO 98/18684 filed by the present Applicant—packaging sheet material 2 is fed through a conventional application unit (not shown)—e.g. an injection-molding unit of the type described in International Patent Application WO 98/18608 filed by the present Applicant—at the output of which packaging sheet material 2 comprises a succession of opening devices 5 equally spaced along an intermediate longitudinal portion of packaging sheet material 2. At the output of the application unit and upstream from sterilizing unit 3, storage (not shown) is conveniently provided to store packaging sheet material 2 and compensate for the different feeds of the two units (step feed and continuous feed respectively).

Machine 1 also comprises a chamber 6 in which packaging sheet material 2 is kept in a sterile-air environment. Chamber 6 comprises a top portion 7, from which sterilizing unit 3 extends downwards, and a bottom portion or tower 8, which extends vertically on one side of top portion 7 and parallel to sterilizing unit 3, and wherein the packaging sheet material, which in the illustrated example comprises a web or strip 2, is folded longitudinally into a cylinder and sealed longitudinally to form a continuous tube (not shown). The tube is filled continuously with the sterilized or sterile-processed food product for packaging, is sealed along equally spaced cross sections, and is subjected to successive mechanical folding operations to form the finished packages.

It should be noted that the sterilizing unit 3 may be located at any convenient position with respect to chamber 6 or even incorporated therein.

Figure 4:
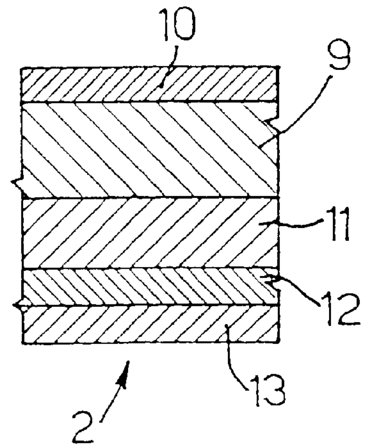
FIG. 4 shows a section of a portion of a packaging sheet material for manufacturing packages of pourable food products.

With reference to FIG. 4, the packaging sheet material 2, shown by way of example, has a multilayer structure and substantially comprises a layer of fibrous material 9, e.g. paper, covered on both sides with respective layers 10, 11 of heat-seal plastic material, e.g. polyethylene. Being used to produce aseptic packages of long-storage products, such as UHT milk, packaging sheet material 2 also comprises, on the side eventually contacting the food product, a layer of oxygen and light barrier material defined, for example, by a sheet of aluminum 12, which in turn is covered with a further layer 13 of heat-seal plastic material, e.g. polyethylene. As mentioned above, the packaging sheet material may also be constituted by a single or multi-layer plastics material, polymeric material, mineral-filled polymers, etc.

Each opening device 5 (FIG. 1) comprises in known manner a base portion 15 fixed to packaging sheet material 2 and a cap portion 16 hinged laterally to and closed on base portion 15.

An important aspect of the present invention is that sterilizing unit 3 comprises two known electron irradiation sources 20 located on opposite sides of packaging sheet material 2 and simultaneously activated for directing respective electron beams, having an energy at most equal to 100 keV, onto opposite faces 2*a*, 2*b* of the packaging sheet material 2.

In the example shown, irradiation sources 20 are aligned with each other in a direction perpendicular to sheet packaging material 2. Alternatively, irradiation sources 20 may even be offset with respect to each other.

The irradiation sources 20 are preferably incorporated in respective fixed housings 21, between which packaging sheet material 2 to be sterilized, and already fitted with auxiliary items, e.g. opening devices 5, is fed.

Figure 2:
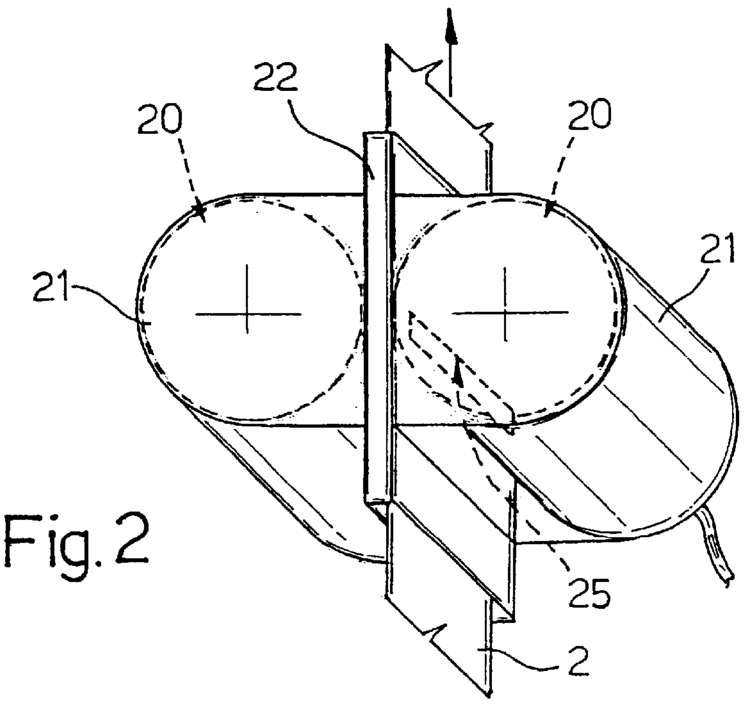
FIG. 2 shows an enlarged view in perspective of the FIG. 1 sterilizing unit.

With particular reference to FIGS. 1 and 2, housings 21 are fixed to the structure of packaging machine 1 and cooperate on opposite sides with a thin, box-shaped guide member 22 fixed between supporting members 21 and through which, in use, packaging sheet material 2 for sterilizing is fed.

Each irradiation source 20 comprises a tubular enclosure 24 having an axis parallel to the plane of the packaging sheet material 2 and perpendicular to path P, and which is kept under vacuum and has an aperture 25 facing material 2 and closed by a window foil 26 which is easily penetrated by electrons. Window foil 26 is constituted, for example, by a sheet of material such as titanium, aluminum, silicon, etc., having a thickness of a few $\mu$m, e.g., 2–35 $\mu$m, and preferably 2–8 $\mu$m.

Figure 3:
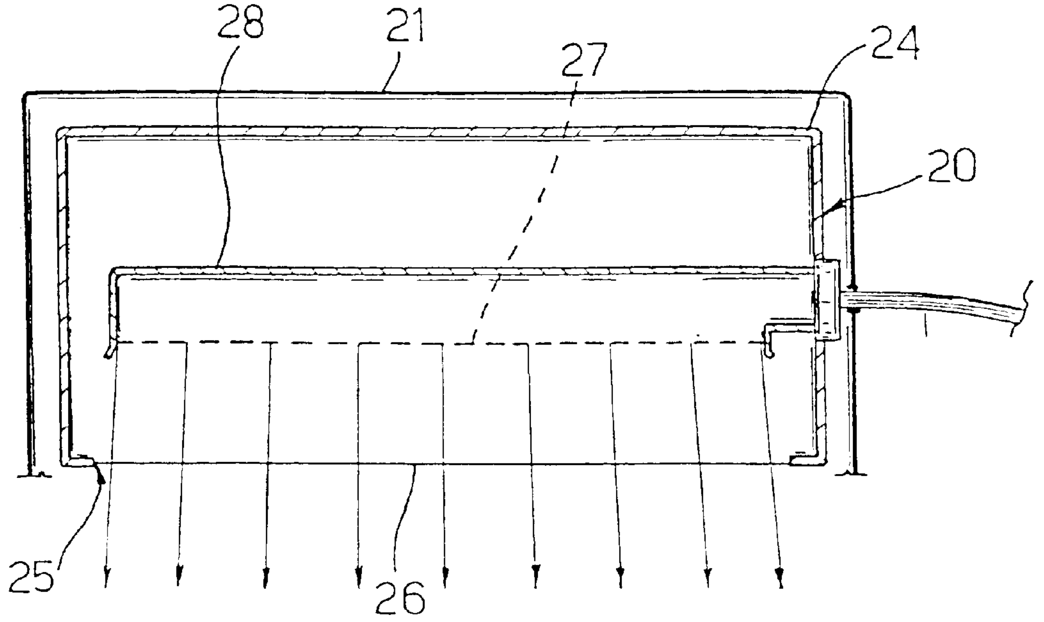
FIG. 3 shows a larger-scale section of a detail of the FIG. 1 sterilizing unit.

Each irradiation source 20 also comprises an electron-emitting member such as, e.g., a tungsten filament 27 (shown schematically by the dash line in FIG. 3), which, in the illustrated example, is housed inside a casing 28 in turn fitted inside enclosure 24, and is heated to emit electrons. Any other electron emitting means may be used.

In use, the electrons are accelerated, in the form of a beam between the filament 27 at negative potential and the window foil 26 which is at ground potential.

In particular, the electrons emitted are vacuum accelerated into beams directed on to sheet packaging material 2 by respective electric fields generated by potential differences of 90 kV or less and preferably less than 80 kV.

The electrons reach their maximum speed inside the vacuum environment defined by enclosure 24, and decelerate and gradually lose part of their energy on colliding with the atoms constituting window foil 26 and sheet packaging material 2.

In the example shown, the energy produced by the electron beams striking sheet packaging material 2 kills any microorganisms in the material.

Given their low energy level (100 keV), the electron beams generated by irradiation sources 20 penetrate sheet packaging material 2 to a depth of a few $\mu$m, which is sufficient to ensure surface sterilization of sheet packaging material 2 on both faces 2*a*, 2*b*, while at the same time minimizing the effect of radiation on the packaging material itself.

Unit 3 also comprises a shielding member 30 (indicated by the dash line in FIG. 1) fixed to the structure of packaging machine 1 and in turn comprising a first portion 31 surrounding housings 21 of electron irradiation sources 20, and a substantially L-shaped second portion 32 extending downwards from portion 31 and enclosing guide roller 4 and the portion of packaging sheet material 2 extending between roller 4 and electron irradiation sources 20. Portions 31, 32 are all shielding but other solutions are possible.

Using electron acceleration potentials of less than 90 kV, shielding member 30 may be made indifferently of steel of less than 20 mm thickness—e.g. 12 mm with an acceleration potential Va of 75 kV or of lead of unit mm thickness—e.g. 2 mm with an acceleration potential Va of 75 kV, or 1 mm with an acceleration potential Va of 50 kV. Tests have shown shielding members 30 formed as described above to be capable of protecting the area around irradiation sources 20 from X-rays produced as a secondary effect of electron absorption by packaging sheet material 2 or parts of packaging machine 1.

The advantages of sterilizing unit 3 according to the present invention will be clear from the foregoing description.

In particular, by using two irradiation sources 20 generating respective low-voltage electron beams directed on to opposite faces 2*a*, 2*b* of sheet packaging material 2 and having an energy of at most 100 keV, each beam penetrates the packaging material to a depth of a few $\mu$m, which, as stated, is sufficient to ensure surface sterilization of both opposite faces of the packaging material, while at the same time minimizing any possible alteration of the packaging material, and so preventing the packaging material from acquiring an unpleasant taste which may be transmitted to the food product.

Furthermore, using electron beams, the sterilizing system described leaves no residue on the processed materials, and may therefore be used to sterilize packaging sheet material (2) with items applied thereto such as pre-applied opening devices (5). This affords enormous advantages in terms of production, by opening devices 5 being much easier and cheaper to apply directly to packaging sheet material 2 than to the finished packages. Moreover, no additional means are required for removing from the packaging material the sterilizing agent normally used in known units of the type described previously.

Sterilizing unit 3 is particularly effective, by the electron beams emitted being capable of reaching any surface or irregularity of opening devices 5.

Finally, the output capacity of sterilizing unit 3 may be increased easily with no alterations to the unit required.

Clearly, changes may be made to sterilizing unit 3 as described and illustrated herein without, however, departing from the scope of the accompanying claims.

The principles, preferred embodiments and manner of use of the present invention have been described in the foregoing specification. However, the invention of which is intended to be protected is not to be construed as limited to the particular embodiments described. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the invention be embraced thereby.

What is claimed is:

1. A method of sterilizing sheet packaging material for producing sealed packages of pourable food products, comprising the step of:

irradiating the packaging material with electrons by directing on to opposite faces of said sheet packaging material respective low-voltage electron beams, each having an energy of at most 100 keV, wherein the electrons do not completely penetrate the depth of the sheet packaging material.

2. The method as claimed in claim 1, further comprising the step of directing said electron beams simultaneously on to said opposite faces of said sheet packaging material.

3. The method as claimed in claim 1, wherein said step of directing each said electron beam comprises the steps of irradiating electrons and accelerating said electrons on to said opposite faces of said sheet packaging material.

4. The method as claimed in claim 3, wherein said step of accelerating said electrons is performed by applying an electric field generated by a potential difference of 90 kV or less.

5. The method as claimed in claim 4, wherein said potential difference is less than 80 kV.

6. The method as claimed in claim 1, wherein said sheet packaging material having a number of pre-applied auxiliary members.

7. The method as claimed in claim 1, wherein said sheet packaging material being in the form of a continuous web.

* * * * *